US005613488A

United States Patent [19]

Schwichtenberg et al.

[11] Patent Number: 5,613,488

[45] Date of Patent: Mar. 25, 1997

[54] CHEMICAL OXYGEN GENERATOR BREATHING DEVICE WITH THE EXHALATION BAG WITHIN THE INHALATION BAG

[75] Inventors: Michael Schwichtenberg; Volker Hünnebeck, both of Berlin, Germany

[73] Assignee: Auergesellschaft GmbH, Germany

[21] Appl. No.: 413,184

[22] Filed: Mar. 30, 1995

[30] Foreign Application Priority Data

Apr. 2, 1994 [DE] Germany .......................... 44 11 560.1

[51] Int. Cl.$^6$ ......................... A61M 15/00; A61M 16/00; A62B 7/08; A62B 21/00

[52] U.S. Cl. ................................ 128/202.26; 128/205.13; 128/205.17

[58] Field of Search ........... 128/202.26, 205.27–205.29, 128/201.22–201.28, 204.15, 204.26, 205.13–205.18, 205.25, 205.22, 204.18; 422/120, 122, 164, 165, 167; 423/579, 582, 641

[56] References Cited

U.S. PATENT DOCUMENTS

| | | | |
|---|---|---|---|
| 1,474,205 | 11/1923 | Mase . | |
| 3,692,026 | 9/1972 | Tepper et al. | 128/202.26 |
| 4,019,509 | 4/1977 | Li et al. | 128/202.26 |
| 4,154,234 | 5/1979 | Baker | 128/205.17 |
| 4,157,091 | 6/1979 | Pampuch | 128/202.26 |
| 4,163,448 | 8/1979 | Grouard | 128/205.12 |
| 4,186,735 | 2/1980 | Henneman et al. | 128/201.25 |
| 4,209,491 | 6/1980 | Rich, III | 128/202.26 |
| 4,301,792 | 11/1981 | Pasternack | 128/202.26 |
| 4,423,723 | 1/1984 | Winkler et al. | 128/205.12 |
| 4,440,162 | 4/1984 | Sewell et al. | 128/202.26 |
| 4,498,470 | 2/1985 | Warncke | 128/202.26 |
| 4,774,942 | 10/1988 | Moellers | 128/205.28 |
| 4,811,732 | 3/1989 | Hartung | 128/205.17 |
| 4,879,996 | 11/1989 | Harwood, Jr. et al. | 128/205.17 |
| 5,048,517 | 9/1991 | Pasternack | 128/205.28 |
| 5,311,861 | 5/1994 | Miller | 128/204.26 |

FOREIGN PATENT DOCUMENTS

| | | | |
|---|---|---|---|
| 2471313 | 6/1981 | France | 128/205.28 |
| 1901243 | 8/1970 | Germany . | |
| 2635376 | 2/1978 | Germany . | |
| 4023013 | 1/1991 | Germany . | |
| 4126685 | 2/1993 | Germany . | |
| 4137331 | 5/1993 | Germany . | |

*Primary Examiner*—Kimberly L. Asher

*Attorney, Agent, or Firm*—Reed Smith Shaw & McClay

[57] ABSTRACT

A chemical oxygen device having one or more $CO_2$-bonding and $O_2$-releasing chemical canisters (2) arranged in a housing (1); a breathing bag (3) for the exhaled air, which itself is arranged in a breathing bag (7) for the inhaled air; an inhalation valve (4); an exhalation valve (5); and a particle filter (6). The usage conditions of chemical oxygen devices is improved by reducing breathing resistances and by an indication of consumption indication in which, at any time, the supply of breathing gas still available is indicated. A bellows (8) is arranged between the breathing bag (3) and chemical canisters (2) to reduce the breathing resistances and the particle filter (6) is arranged at the input of the breathing bag (7). The bellows (8) is connected to an evaluation unit (9), via which the wearer of the chemical oxygen device can check at any time the supply of breathing gas still available.

5 Claims, 1 Drawing Sheet

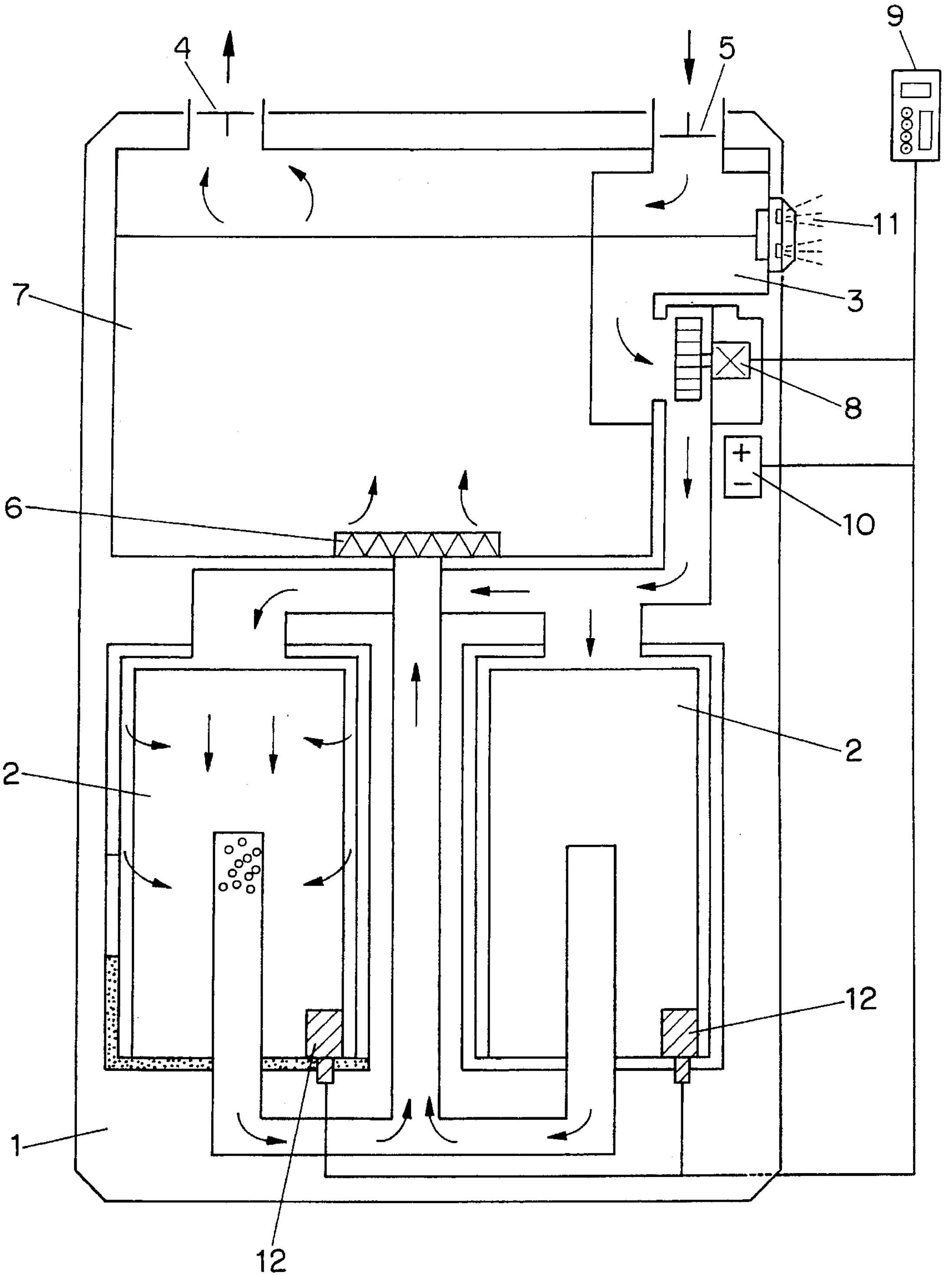
9
4
5
11
3
7
8
10
6
2
2
12
1
12

CHEMICAL OXYGEN GENERATOR BREATHING DEVICE WITH THE EXHALATION BAG WITHIN THE INHALATION BAG

BACKGROUND OF THE INVENTION

The invention relates to a chemical oxygen device comprising: one or more $CO_2$-bonding and $O_2$-releasing chemical canisters arranged in a housing; a breathing bag for exhaled air, being arranged in a breathing bag for inhaled air; an inhalation valve; an exhalation valve and a particle filter.

FIELD OF THE INVENTION

According to the prior art, chemical canisters for respiratory protective devices are known. Such a chemical canister is described in DE 26 35 376 C2.

In the variant described in DE 26 35 376 C2, the chemical, bounded by an upper space and a lower space, is perfused by the exhaled air through a frontal shell surface of the volume occupied by the chemical and, as breathable air, enters a breathing bag via a central tube (the tube having holes provided on its periphery).

A shortcoming of the above-described variant is that, in addition to insufficient perfusion of the chemical and the consequent limit placed on the usage time of such devices due to incomplete utilization of the chemical during the usage period, there is a significant burden on the wearer of the respirator because of the need to overcome high breathing resistances.

An improved chemical canister for respirators, that overcomes the shortcoming of insufficient perfusion and thus results in better utilization of the chemical, is known from DE 41 26 685. According to this solution, two tube connections are arranged in the chemical canister so that even boundary regions of the chemical are perfused by the exhaled air with greater reliability.

A shortcoming of the solution disclosed in DE 41 26 685 is that, in this improved solution, a usage time that is independent of the usage conditions must be established with a safety margin. Further, high breathing resistances must also be overcome by the user of this respirator.

In commercial chemical oxygen devices, the particle filter is arranged directly on the inhalation valve. In devices that function according to the principle of fluctuating respiration (DE 41 37 331), a heat exchanger is also required. This means that, during inhalation, resistance associated with the filter and/or heat exchanger must be overcome by the user.

The prior art also includes chemical oxygen devices that either are furnished with a time-controlled consumption indicator (DE 19 01 243) or determine consumption based on the number of breaths of the wearer (US 14 74 205). For safety reasons, incomplete utilization of the chemical during the usage period must always be accounted for in these two prior art examples, since, invariably, both time control and control via breaths can only occur independently of usage conditions.

A chemical oxygen device is also known in which a ventilator is used to more reliably guide the exhaled air to the chemical (DE 40 23 013). This solution has the shortcoming that all of the exhaled air is involved in oxygen production (i.e., demand-based preparation of oxygen does not occur, but rather the possibility exists that too much oxygen will be produced). The ventilator does not contribute to a reduction in breathing resistance, but only helps improve perfusion of the chemical with exhaled air.

The underlying objective of the invention is therefore to improve the usage conditions of chemical oxygen devices by reducing breathing resistances and by providing a consumption reading that indicates, at all times, the supply of breathing gas still available.

SUMMARY OF THE INVENTION

The advantages enjoyed in accordance with the invention reside in the fact that a predetermined amount of chemical is optimally utilized for oxygen production independently of the usage conditions so that a longer use time for the respirator is possible.

Additional advantageous embodiments of the invention follow from: an energy source, provided for the bellows, that is being connected to the evaluation unit and arranged in the housing; chemical canisters designed as double-jacketed containers for receiving coolant and that contain ignition devices connected with the evaluation unit; and an overpressure valve arranged in the exhalation bag.

BRIEF DESCRIPTION OF THE DRAWING

The invention is further explained with reference to a practical example depicted in the drawing.

DESCRIPTION OF THE PREFERRED EMBODIMENT

The figure shows a schematic view of a practical example of the chemical oxygen device according to the invention. As is apparent from the figure, the chemical oxygen device is operated in a respiration circuit. The device includes a wearable housing (1) in which two chemical canisters (2), which contain a chemical in the form of a $CO_2$-bonding and $O_2$-liberating substance (for example, potassium peroxide[1]), are arranged next to each other.

[1][Translator's Note: German text speaks of potassium "hyperoxide" in this case probably a mixture of K202 (peroxide) and K02 (superoxide).]

The chemical canisters (2) are connected, on the exhalation side, to a breathing bag (3) for exhaled air. At the input of breathing bag (3), an exhalation valve (5) is arranged. Further, a bellows (8) and an overpressure valve (11) are present on the wall of breathing bag (3). On the inhalation side, the chemical canisters (2) are connected to a breathing bag (7) for inhaled air. At the input of breathing bag (7), a particle filter (6) is arranged, and the output, an inhalation valve (4) is arranged. An energy source (10) (for example, a battery or storage cell) is arranged in housing (1) as an energy supply for bellows (8).

Ignition devices (12) are arranged on the bottom of the chemical canisters (2) to ignite the chemical in the canisters. Bellows (8), energy source (10) and the ignition devices are electrically connected to an evaluation unit (9).

The perfusion of the individual components of the chemical oxygen device is depicted by arrows in the drawing. During exhalation, the user of the inventive chemical oxygen device only overcomes the breathing resistance of the exhalation valve (5). Bellows (8) assumes the task of overcoming the breathing resistances of chemical canisters (2) and particle filter (6) by displacing under the power of energy source (10) and thus expediting the passage of the patient's breath by temporarily boosting its flowrate until it encounters chemical canisters (2) and particle filter (6), whereupon the attendant resistance will again decrease the flowrate of the patient's breath.

By the arrangement of particle filter (6) at the input of breathing bag (7) in accordance with the invention, a situation was achieved in which the user need only overcome the breathing resistance of the inhalation valve during inhalation and need not overcome the additional breathing resistance of particle filter (6), which otherwise would have been necessitated by connection of the inhalation valve and filter (as is common in the solutions of the prior art).

The usage conditions of the inventive chemical oxygen device are further improved by the evaluation unit (9), which indicates the available supply of breathing gas at any point in time. The reading can be effected, for example, by evaluation of the parameters of bellows (8) and of the consumption of the chemical (based on the supply of chemical still available).

The evaluation unit also serves the purposes of indicating the charging state of energy source (10) and of initiating initial ignition via ignition devices (12).

Evaluation unit (9) will preferably be suitably configured to undertake the attendant functions discussed hereinabove and, as such, will preferably include suitable visual or audible indicators, insignia and/or other media for affording the user the capability of instantaneously ascertaining the various parameters discussed hereinabove.

The chemical canisters (2) are designed as double-jacketed containers equipped with a coolant for cooling the warm inhaled gas formed by exothermic reaction.

What is claimed is:

1. A chemical oxygen device comprising:

a housing;

one or more $CO_2$-bonding and $O_2$-releasing chemical canisters disposed in said housing;

a first breathing bag for inhaled air disposed in said housing, said first breathing bag comprising an input, an inhalation valve and a particle filter, the particle filter operationally associated with the input;

a second breathing bag for exhaled air disposed in said first breathing bag, said second breathing bag comprising an exhalation valve;

a bellows arranged between said second breathing bag and said one or more canisters; and an evaluation unit connected with said bellows.

2. The device of claim 1, further comprising an energy source disposed in said housing, said energy source connected to said bellows and said evaluation unit.

3. The device of claim 1 wherein each of said one or more canisters comprises a double-jacketed canister.

4. The device of claim 1 wherein each of said one or more canisters comprises an ignition device connected to said evaluation unit.

5. The device of claim 1 wherein said second breathing bag further comprises an overpressure valve.

* * * * *